United States Patent [19]
Figuly

[11] Patent Number: 5,270,402
[45] Date of Patent: * Dec. 14, 1993

[54] HYPERBRANCHED POLYESTERS

[75] Inventor: Garret D. Figuly, Wilmington, Del.

[73] Assignee: E. I. Du Pont de Nemours and Company, Wilmington, Del.

[*] Notice: The portion of the term of this patent subsequent to Aug. 4, 2009 has been disclaimed.

[21] Appl. No.: 944,586

[22] Filed: Sep. 14, 1992

Related U.S. Application Data

[62] Division of Ser. No. 865,599, Apr. 9, 1992, Pat. No. 5,183,862, which is a division of Ser. No. 548,681, Jun. 22, 1990, Pat. No. 5,136,014.

[51] Int. Cl.$^5$ .............................................. C08F 20/00
[52] U.S. Cl. .................................. 525/440; 528/272; 528/292; 528/298; 528/302; 528/303; 528/306; 528/308; 525/437; 524/601; 524/602; 524/603; 524/607; 524/606; 424/486
[58] Field of Search ............... 528/272, 292, 298, 302, 528/303, 306, 308; 525/437, 440; 524/601, 602, 603, 607, 608; 424/486

[56] References Cited

U.S. PATENT DOCUMENTS

| | | | |
|---|---|---|---|
| 3,669,939 | 6/1972 | Baker et al. | 528/361 |
| 4,289,872 | 9/1981 | Denkewalter et al. | 528/328 |
| 4,360,646 | 11/1982 | Denkewalter et al. | 525/420 |
| 4,410,688 | 10/1983 | Denkewalter et al. | 528/328 |
| 4,507,466 | 3/1985 | Tomalia et al. | 528/332 |
| 4,558,120 | 12/1985 | Tomalia et al. | 528/363 |
| 4,568,737 | 2/1986 | Tomalia et al. | 528/332 |
| 4,587,329 | 5/1986 | Tomalia et al. | 528/363 |

FOREIGN PATENT DOCUMENTS

| | | |
|---|---|---|
| 8402705 | 7/1984 | PCT Int'l Appl. |
| 2132626 | 7/1984 | United Kingdom |

OTHER PUBLICATIONS

Flory, J. Amer. Chem. Soc., 74, 2718 (1952).
Flory, "Principles of Polymer Chemistry", Cornell University Press, 361-370 (1953).
Maciejewski, J. Macromol. Sci.-Chem., A17(4), 689-703 (1982).
Kricheldorf et al., Polymer 11, 23, 1821-1829 (1982).
Aharoni et al., Polymer Comm., vol. 24, 132-136 (1983).
Aharoni et al., Macromolecules, 15, 1093-1098 (1982).

*Primary Examiner*—John Kight, III
*Assistant Examiner*—S. A. Acquah

[57] ABSTRACT

This invention relates to hyperbranched, functional polyesters.

8 Claims, No Drawings

HYPERBRANCHED POLYESTERS

This is a division of application Ser. No. 07/865,599, filed Apr. 9, 1992, now U.S. Pat. No. 5,183,862, which is a division of application Ser. No. 07/548,681, filed Jun. 22, 1990, now U.S. Pat. No. 5,136,014.

FIELD OF THE INVENTION

This invention relates to hyperbranched, functional polyesters.

BACKGROUND OF THE INVENTION

Baker et al., U.S. Pat. No. 3,669,939 disclose highly branched condensation polymers prepared from polyhydroxymonocarboxylic acids $(OH)_nR—CO_2H$ wherein R is a hydrocarbon radical of up to 22 carbon atoms optionally interrupted by a heteroatom, and n is 2-6. Monomers disclosed as particularly suitable are those of the formula $(HOCH_2)_2—C(R^3)CO_2H$ wherein $R^3$ is alkyl or $—CH_2OH$. Aromatic monomers are not exemplified.

P. J. Flory, J. Amer. Chem. Soc., 74, 2718 (1952), "Principles of Polymer Chemistry", Cornell University Press, 1953, pp. 361-370, discusses the theory of condensation polymerization of so-called $AB_n$-type monomers wherein A and B functions condense together to form branched high polymers which attain high molecular weight without gelation. The theory predicts that polymerization of such monomers containing one A and Bn functions leads to randomly branched polymers containing one unreacted A function and $(n-1)x+1$ unreacted B functions where x is the number of monomer units, said polymers being more polydisperse the higher the degree of polymerization. Examples of monomers of this type given by Flory are benzyl halides $XCH_2—C_6H_5$, alkali metal salts of trihalophenols and D-glucose; the polymers are said to be soluble, non-crystalline and fusible when correctly prepared. Fully aromatic monomers of the $AB_n$-type, or polymers therefrom, are not disclosed.

Maciejewski, J., Macromol. Sci.-Chem., A17 (4), 689 (1982) describes his concept of so-called shell topological compounds, preparation of which includes polymerization of a monomer of the $XRY_n$-type, wherein n is at least 2. Such polymerization results in a "cascade branched (uncrosslinked) molecule of spherical structure". Equations are provided which correlate, among other properties, molecular weight with sphere diameter. Although monomers employed in the present invention are of the $XRY_n$-type, the reference does not suggest polymerization of arylene monomers Or the physical properties of the polyarylenes therefrom.

Tomalia et al., U.S. Pat. Nos. 4,587,329; 4,568,737; 4,588,120; 4,507,466 and WO 84/02705 disclose dense star polymers containing core, core branches and terminal groups. These polymers are built up, layer after layer, from a core substance by selective condensation of functional groups; each successive layer becomes a core for the subsequent layer. Only aliphatic polyamides and polyethers are exemplified. The monomers are of the $AB_n$-type and the polymers therefrom are said to be Q soluble and to have a molecular volume less than 80% of that of a conventional extended star polymer made from similar materials, molecular diameters being less than 2000 angstrom units.

U.K. Patent Application GB 2,132,626 discloses a method for producing aromatic polyesters by polycondensation of A: aromatic hydroxycarboxylic acids, or A with B: one or more compounds selected from aromatic dicarboxylic acids and C: one or more compounds selected from aromatic diphenols, and on said polycondensation, adding D: one or more compounds selected from the group consisting of aromatic trihydroxy compounds, aromatic dihydroxy-monocarboxylic acids and aromatic monohydroxydicarboxylic acids.

Kricheldorf et al., Polymer [11], 23, 1821 (1982) disclose the preparation of branched poly(3-hydroxybenzoate) by condensation of 3-(trimethylsiloxy)benzoyl chloride and 3,5-(bistrimethylsiloxy)benzoyl chloride, said polycondensate remaining uncrosslinked regardless of degree of conversion.

The prior art does not disclose soluble, highly branched polyesters prepared by self-polycondensation of $AB_n$-type monomers wherein n is at least 2 and wherein B moieties contain a terminal carboxylic acid group or derivative thereof, or wherein either A or B is a carboxyl or hydroxyl-terminated moiety which is an aromatic or aliphatic amino. By soluble is meant that the polyester is soluble to at least 5% in solvents such as tetrahydrofuran, dimethylacetamide, acetone, chloroform or hexafluoroisopropanol.

SUMMARY OF THE INVENTION

The present invention provides:

(1) the soluble, hyperbranched polyester having at least one branch per 10 monomer units prepared in a process comprising polycondensation of one or more monomers of the formula:

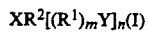

$$XR^2[(R^1)_mY]_n(I)$$

wherein;

$R^1$ is a divalent $C_{1-12}$ hydrocarbyl radical which is linear or branched aliphatic, alicyclic, aromatic or mixed aromatic-aliphatic;

$R^2$ is a $C_{1-12}$ hydrocarbyl radical having a valence of $(n+1)$, said radical being linear or branched aliphatic, alicyclic, aromatic or mixed aromatic-aliphatic, or $R^3N$ wherein $R^3$ is defined as for $R^1$;

either of $R^1$, $R^2$ or $R^3$ optionally also containing substituents that are unreactive under processing conditions, i.e., the polycondensation and recovery conditions, X and Y are terminal functions selected from $—CO_2R'$ and $—OR''$ wherein R' is H Or $C_{1-12}$ alkyl and R'' is H Or OC(O)R;

m is 0 or 1; and n is an integer and is at least 2;

with the provisos that:

(i) both X and Y are not $—CO_2R'$ or $—OR\Delta$;

(ii) no X or Y function is adjacent to another X or Y function;

(iii) when $R^2$ is an aliphatic hydrocarbyl radical, Y is $—CO_2R'$; and (iv) when $R^2$ is $R^3N$, m is 1.

This invention also provides:

(2) the soluble hyperbranched polyester prepared from one or more monomers of Formula I wherein residual terminal functions (X and Y groups) have been chemically capped;

(3) the hyperbranched polyester of (1) that has been linearly linked or crosslinked;

(4) copolymers of the hyperbranched polyester of (1) with diols or dicarboxylic acids;

(5) a stable dispersion of the soluble hyperbranched polymer of (1), (2) or (4) above;

(6) process of using the soluble hyperbranched polymer of (1), (2) or (4) in a drug delivery system; and (7) process of using the soluble hyperbranched polymer of (1), (2) or (4) as a rheology modifier.

Another embodiment of the invention is the capped polyester produced by capping with a monofunctional capping agent the X and Y functions of a hyperbranched polyester having at least 1 branch per 10 monomer units prepared by conventional polycondensation of one or more monomers of the formula:

$$XR^2[(R^1)_mY]_n \quad (II)$$

wherein:
$R^1$ is a divalent $C_{1-12}$ hydrocarbyl radical which is linear or branched aliphatic, alicyclic, aromatic or mixed aromatic-aliphatic;
$R^2$ is a $C_{1-12}$ hydrocarbyl radical having a valence of $(n+1)$, said radical being linear or branched aliphatic;
either of $R^1$ or $R^2$ optionally also containing substituents that are unreactive under processing conditions;
X is $-CO_2R'$;
Y is $-OR\Delta$;
wherein
$R'$ is H or $C_{1-12}$ alkyl and $R\Delta$ is H or $OC(O)R$;
m is 0 or 1; and
n is an integer and is at least 2;
with the proviso that:
no X or Y function is adjacent to another X or Y function.

This embodiment also covers the above polyester that has been linearly linked or crosslinked or copolymers of the polyester with diols or dicarboxylic acids.

DETAILS OF THE INVENTION

Monomers of Formula I wherein $R^2$ is $R^3N$ are good yield by refluxing the appropriate $\alpha, \beta$ unsaturated alkyl ester with the appropriate amino alcohol in a suitable solvent such as methanol; e.g., $$HOR^3NH_2 + CH_2=CHCOOR' \rightarrow HOR^3N(CH_2CH_2COOR')_2$$

$$NH(R^1OH)_2 + CH_2=CHCOOR' \rightarrow (HOR^1)_2NCH_2CH_2COOR'.$$

Monomers of Formulae I or II wherein $R^2$ is an aromatic moiety are preferably employed as the acyl esters ($R'$ is $OC(O)R'$). Such esters may be prepared from the corresponding alcohols using conventional techniques for acylation, such as, for example, acetic anhydride with sulfuric acid catalyst. Cycloaliphatic monomers of Formulae I or II may be prepared using conventional organic synthetic methods including direct hydrogenation of aromatic rings using an appropriate hydrogenation catalyst. Other monomers of Formulae I and II are known or obvious compounds prepared by conventional methods, e.g., as disclosed in U.S. Pat. No. 3,669,939.

As previously indicated, $R^1$, $R^2$ and $R^3$ can contain substituents, e.g., halogen, lower alkyl, that are not reactive under the polycondensation and recovery conditions.

The soluble hyperbranched polyesters (HBP-1) of the invention are prepared by the conventional self-condensation polymerization of one or more monomers of Formulae I or II wherein said monomers are heated at a temperature in the range of 100° C. to 325° C. with vacuum (0.5 mm Hg; 133 Pa) being applied at the later stages of the polymerization until a viscous melt is obtained. For many monomers, especially aliphatic or alicyclic monomers, a temperature in the range of 100° C. to 280° C. is adequate.

The reaction time is not critical and is that required to complete the desired polymerization, e.g., ranges from less than 30 minutes to several hours. If desired, with some monomers, room temperature polycondensation can be employed and a vacuum is not required.

A polymerization catalyst is not necessary but can be used to shorten reaction time if desired. Conventional catalysts useful for the condensation of carboxylic acids or esters with alcohols or esterified derivatives thereof can be used such as, for example, tetra-n-butyltitanate, tetraisopropyltitanate or hydrated monobutyltin oxide. Such catalysts are effective in the polymerization at a concentration of at least about 0.01 wt%, preferably about 0.1–0.2 wt%.

The polymerization is preferably conducted under an inert atmosphere such as nitrogen, helium, or argon.

The hyperbranched polyesters are normally recovered from the reaction as solids or viscous liquids. The polyesters can be purified by conventional techniques such as recrystallization or extraction.

In preparing soluble hyperbranched polyesters of the invention (HBP-1) from aromatic monomers of Formulae I or II, it is preferred that the reactive terminal carboxyl or hydroxyl functions (X or Y), like or unlike, are not attached to immediately adjacent carbon atoms as steric crowding may inhibit polymerization and branching.

The hyperbranched polyesters HBP-1 contain one X function and numerous Y functions in each polymer molecule; many of which are available for post polymerization reaction with suitable reagents, including capping, linear linking and cross-linking. By "capping" is meant contacting and reacting HBP-1 with a compound (capping agent) containing a functional group which combines chemically with an X or Y function in the hyperbranched polyester; the capped polyester HBP-2 is provided by reaction of some or all of the available HBP-1 functions with capping agent. The capping agent may also contain other substituents which are inert under capping process conditions. Capping agents include polymers and non-polymeric substances. The purpose of capping is normally to: (i) deactivate the X and Y functions; (ii) attach selected molecules to the HBP-1 molecules, for example polymeric "arms", forming star-shaped structures; and/or (iii) replace the X and Y functions with other substituents having increased activity for desired post-polymerization reactions.

Suitable capping agents for HBP-1 wherein the residual Y functions are hydroxyl groups (or reactive derivatives thereof) include, for example, anhydrides (acetic, succinic, maleic), acyl chlorides (acetyl, cinamoyl), isocyanates (allyl, 4-bromophenyl, benzyl, cyclohexyl), and benzylisothiocyanate.

Suitable capping agents for HBP-1 wherein the residual Y functions are carboxyl groups (or reactive derivatives thereof) groups include, for example, bases (alkali metal hydroxides and carbonates), alcohols, isocyanates and acyl chlorides. Capping with bases results in HBP-2 salts having increased solubility in ionizing solvents. Other suitable capping agents will occur to those skilled in the art.

Molecules of hyperbranched polyester HBP-1 may be linearly linked together or cross-linked to form HBP-3 products by reacting the residual X and Y functions in HBP-1 with difunctional reagents such as, for example, diisocyanates (2,4-toluene diisocyanate, 1,6-diisocyanatohexane), diols or diacyl chlorides.

Higher order polymeric structures which can be prepared by the post polymerization processes of capping, linking or crosslinking as just described include, for example: (a) simple end capped hyperbranched polymers (HBP-2) which embrace star polymers (represented schematically by Formula A below) wherein the arms are provided by a capping agent that is monofunctional linear polymer; (b) linearly linked polymers (schematic B below) wherein the hyperbranched polymer molecules act as functionalized "beads" in a chain; and (c) "nodular networks" (schematic C. below) wherein the hyperbranched polymer behaves as a highly functionalized "nodular" junction point for many linear chains.

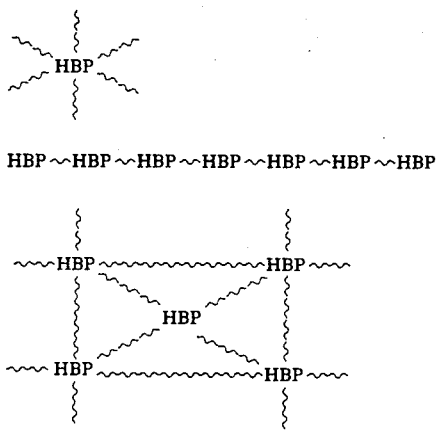

Examples of the above structures have been prepared (Examples 10-13) using a hyperbranched polymer prepared from 2,2-bis(hydroxymethyl)propionic acid. When the hyperbranched polymer product is reacted with 1-2 molar equivalents of a diisocyanate such as 1,6-diisocyanatohexane, the polymer loses solubility in THF but retains it in hexafluoro-isopropanol (HFIP). The inherent viscosity of the reaction product in HFIP increases from 0.15 to 0.32 and the glass transition temperature (Tg) increases from 42° C. to 53° C. It is believed from stoichiometric and steric considerations and product solubility that this material is a "beaded" polymer chain wherein HBP units are linearly linked together. As additional diisocyanate is added, loosely crosslinked structures are prepared which become highly swollen in many solvents but remain insoluble. After approximately 5 equivalents of diisocyanate have been added to the original hyperbranched polymer, a tightly crosslinked structure develops, believed to be a "nodular network", which is only slightly swollen by solvents, exhibits a greatly elevated Tg of 127° C., and is unusually resistant to strong base such as sodium hydroxide, decomposition taking hours as compared to <5 minutes for the original hyperbranched polyester.

Density determinations on the above described products indicate that as the structure becomes more highly crosslinked the hyperbranched polymer nodular network becomes less dense. The overall structure is more open than the original hyperbranched polyester. The resulting voids between nodules should be "lined" with functional groups from the nodules and should be effective in trapping small molecules by means of size and/or chemical reactivity. The highly crosslinked structures of the invention are chemically and mechanically stable and can be used as catalysts, catalyst supports, column packing material for chromatography, or filters.

The polyesters (HBP-1) of the invention are known to be very highly branched for the following reasons:

(i) end group analysis indicates the presence of one X function and a large number of Y functions in each molecule and a number average molecular weight of at least 1500; $^{13}$CNMR measurements on aliphatic HBP have shown 1 branch per 2-3 monomer units;

(ii) clarity of the polymer and the absence of a crystalline melting point, indicating the absence of crystallinity characteristic of linear polyesters;

(iii) high solubility; and (iv) a low inherent viscosity typical of highly branched polymers.

The hyperbranched polyesters HBP-1 may be copolymerized with diols or dicarboxylic acids which are polymerizable by melt polycondensation. The selection of comonomer depends upon the identity of the Y terminal functions. Thus, if Y is —OR$\Delta$ the comonomer should be a dicarboxylic acid; if Y is —CO$_2$R′, the comonomer should be a diol.

It will be apparent to those skilled in the art that the hyperbranched polyesters of the invention can be "tailored" by controlled linking, crosslinking, copolymerization, and/or partial or complete capping to modify functionality, thus optimizing their utility in uses such as catalysts, chromatography packing, or filtering agents.

The comparatively dense, globular, highly functionalized hyperbranched polyesters of the invention are also useful as adhesives, drug delivery agents, rheology control agents in solutions and dispersions for paints and coatings, and as polymeric binders for paints and coatings. Utility of these polymers can be further enhanced by changing end group functionality by means of end capping or by crosslinking the globular structures to produce a highly functionalized "nodular network".

The following experiments illustrate the preparation of monomers of Formula I wherein R$^2$ is R$^3$N.

EXPERIMENT 1

Preparation of HO(CH$_2$)$_2$N(CH$_2$CH$_2$COOCH$_3$)$_2$

Into 50 ml of methanol was added 6.1 g (0.10 mol) of ethanol amine and 20 ml (0.22 mol) of methylacrylate. The resulting mixture was then stirred unheated for 30 min during which time the temperature rose to 35° C. The mixture was then boiled for 4 h, volatiles were removed under high vacuum at room temperature and 21.5 g (92%) of alcohol diester as a colorless oil was obtained. $^1$H NMR (CDCl$_3$): 2.7 (m, 10, CH$_2$'s of acrylate arms and next to N), 3.1 (s, 1, OH), 3.6 (t, 2, CH$_2$ next to OH), 3.7 (s, 6, CH$_3$'s).

IR (neat): 3450 cm$^1$ (br, w, OH), 1740 cm$^1$ (s, C=O).

Elemental Analysis for C$_{10}$H$_{19}$NO$_5$:

| Calculated: | C, 51.50; | H, 8.15; | N, 6.01 |

| Found: | C, 51.80; | H, 8.30; | N, 6.20. |

EXPERIMENT 2

Preparation of HO(CH$_2$)$_3$N(CH$_2$CH$_2$COOCH$_3$)$_2$

The procedure of Experiment 1 was repeated using 7.5 g (0.10 mol) of 3-amino-1-propanol and yielded 22.5 g (91%) of alcohol diester as a colorless oil.

$^1$H NMR (CDCl$_3$): 1.7 (p, 2, HOCH$_2$CH$_2$CH$_2$(H$_2$N), 2.7 (m, 10, CH$_2$'s of acrylate arms and next to N), 3.7 (s and m, 9, OH, CH$_2$ next to OH and CH$_3$'s).

IR (neat): 3450 cm$^{-1}$ (br, w, OH), 1735 cm$^{-1}$ (s, C=O).

Elemental Analysis for C$_{11}$H$_{21}$NO$_5$:

| Calculated: | C, 53.44; | H, 8.50; | N, 5.67 |
| Found: | C, 53.35; | H, 8.51; | N, 5.85. |

EXPERIMENT 3

Preparation of HO(CH$_2$)$_5$N(CH$_2$CH$_2$COOCH$_3$)$_2$

The procedure of Experiment 1 was repeated using 10.3 g (0.10 mol) of 1-amino-5-pentanol and yielded 24.6 g (89%) of alcohol diester 3 as a yellow oil.

$^1$H NMR (CDCl$_3$): 1.4 (m, 6, HOCH$_2$CH$_2$CH$_2$CH$_2$CH$_2$(H$_2$N), 2.5 (m, 10, CH$_2$'s of acrylate arms and next to N), 3.2 (s, 1, OH), 3.6 (t, 2, CH$_2$ next to OH), 3.7 (s, 6, CH$_3$'s).

IR (neat): 3450 cm$^{-1}$ (br, w, OH), 1740 cm$^{-1}$ (s, C=O).

Elemental Analysis for C$_{13}$H$_{25}$NO$_5$:

| Calculated: | C, 56.73; | H, 9.09; | N, 5.09 |
| Found: | C, 56.99; | H, 9.07; | N, 4.83. |

EXPERIMENT 4

Preparation of p-HOC$_6$H$_4$CH$_2$CH$_2$N(CH$_2$CH$_2$COOCH$_3$)$_2$

The procedure of Experiment 1 was repeated using 13.7 g (0.10 mol) fo tyramine and yielded 29.6 g (96%) of alcohol diester as a dark brown oil.

$^1$H NMR (CDCl$_3$): 2.6 (m, 12, all CH$_2$'s), 3.7 (s, 6, CH$_3$'s), 6.4 (s, 1, OH), 6.9 (dd, 4 ArH, J=8.8 Hz).

IR (neat): 3420 cm$^{-1}$ (br, w, OH), 1735 cm$^{-1}$ (s, C=O).

Elemental Analysis for C$_{16}$H$_{23}$NO$_5$:

| Calculated: | C, 62.14; | H, 7.44; | N, 4.53 |
| Found: | C, 62.39; | H, 7.69; | N, 4.55. |

EXPERIMENT 5

Preparation of (HOCH$_2$CH$_2$)$_2$NCH$_2$CH$_2$COOCH$_3$

The procedure of Experiment 1 was repeated except 70 ml of methanol and 10 ml (0.1 mol) of methylacrylate were used with 10.5 g (0.10 mol) of diethanol amine to yield 17.2 g (90%) of ester diol as a colorless oil. $^1$H NMR (CDCl$_3$): 2.6 (m, 8, CH$_2$'s of acrylate arm and next to N), 3.6 (m, 4, CH$_2$'s next to OH's), 3.7 (s, 3, CH$_3$), 3.9 (s, 2, OH's).

IR (neat): 3400 cm$^{-1}$ (br, m, OH), 1735 cm$^{-1}$ (s, C=O).

Elemental Analysis for C$_8$H$_{17}$NO$_4$:

| Calculated: | C, 50.26; | H, 8.90; | N, 7.33 |
| Found: | C, 50.02; | H, 8.95; | N, 7.61. |

In the following embodiments of the invention, parts and percentages are by weight and temperatures are in degrees Celsius unless otherwise specified.

Terminal functions X and Y were determined as follows:

Hydroxyl end groups: A 1 g sample of HBP is dissolved in 20 ml of dry nitrobenzene, stirred at about 170° C. until dissolved, then reacted with 2 ml of 3,5-dinitrobenzoylchloride at 115° C. for 10 min. The reaction mixture is removed from the heat source, stirred 1 min, treated with 1 ml of a 1:1 mixture of pyridine and water, heated a further minute at 115° C., then cooled to room temperature. The solution is treated with 25 ml of o-cresol and 25 ml of chloroform, then titrated with 0.1 N ethanolic potassium hydroxide. A blank is run by the above procedure, omitting only the HBP sample.

Hydroxyl ends, equivalents per 10$^6$ g HBP =

$$\frac{(B + C) - A \times 1000}{\text{sample weight, g}}$$

where

A=ml of KOH required x N of KOH;

B=ml of KOH required for blank x N of KOH;

C=COOH end groups × g sample used for OH ends/1000.

Carboxyl end groups: A 1 g sample of HBP is dissolved, with stirring, in 50 ml of distilled o-cresol at 150° C. The solution is removed from the heat source, stirred a further minute, treated with 4 drops of bromophenol blue Na salt in 1% ethanol and titrated with 0.04 N KOH in benzyl alcohol.

Carboxyl ends, equivalents per 10$^6$ g HBP =

$$\frac{A - B \times 1000}{\text{sample wt, g}}$$

where

A=ml of KOH required x N of KOH;

B=ml of KOH required for blank x N of KOH.

Inherent viscosity is in dl/g, measured in accordance with W. R. Sorenson and Y. W. Campbell, "preparative Methods of Polymer Chemistry", Interscience, 2nd Ed. (1968), p. 44, on a solution of 0.5 g of HBP in 100 ml of m-cresol at 30° C., unless otherwise indicated.

Thermal transitions such as melting point and glass transition point (Tg) were measured with a Du Pont Model 9900 Differential Scanning Calorimeter (DSC) in accordance with B. Wunderlich, "Thermal Analysis", published by Rensselaer Polytechnic Institute (1981).

Density was measured by the Gradient Tube method ASTM D 15056-68.

Degree of branching was determined by carbon nuclear magnetic resonance (CNMR).

HBP products were considered "soluble" in a given solvent if an at least 3 to 5 wt% solution of the polymer could be prepared.

EXAMPLE 1

Polymerization of $H_3COOCCH_2CH_2N(CH_2CH_2OH)_2$

Into a 250 ml round bottom 3-necked flask equipped with a mechanical stirrer, $N_2$ inlet, reflux-distillation condenser and Wood's metal bath was added 7 g (0.037 mol) of the monomer prepared in Experiment 5 and 2-3 drops of Fascat ™ 4102 tin based polymerization catalyst. The mixture was heated using the indicated cycle until noticeable melt viscosity was attained. The results are given below.

| Temp (°C.) | Time (h) | Yield | Tg | ηinh |
|---|---|---|---|---|
| 100 | 3 | | | |
| 100 | 2* | | | |
| 125 | 1* | 83% | −36° C. | 0.11 |

*Vacuum applied (<0.5 mm)

EXAMPLES 2-5

Polymerization of $HOR^3N(CH_2CH_2CO_2CH_3)_2$

General Procedure

Into a 250 ml round bottom 3-necked flask equipped with a mechanical stirrer, $N_2$ inlet, reflux-distillation condenser and Wood's metal bath was added one of the monomers prepared in Experiments 1-4 and 2-3 drops of Fascat ™ 4102. The mixture was heated using the indicated cycle until noticeable melt viscosity was attained. The results are given in Table 1.

TABLE 1

| Ex. | $R^3$ | Wt | Temp. | Time (h) | Yield | Tg | ηinh |
|---|---|---|---|---|---|---|---|
| 2 | $(CH_2)_5$ | 8.0 g | 125 | 2 | | | |
| | | | 150 | 1 | | | |
| | | | 175 | 0.5 | | | |
| | | | 175 | 0.5* | 67% | −48 | — |
| 3 | $C_6H_4(CH_2)_2$ | 9.0 g | 100 | 1 | | | |
| | | | 150 | 2 | | | |
| | | | 150 | 2* | 50% | 58 | 0.09 |
| 4 | $(CH_2)_3$ | 7.0 g | 100 | 0.75 | | | |
| | | | 125 | 0.50 | | | |
| | | | 150 | 1.5 | | | |
| | | | 150 | 1.5* | 83% | −39 | 0.13 |
| 5 | $(CH_2)_2$ | 7.0 g | 100 | 2 | | | |
| | | | 100 | 2* | 85% | −45 | 0.08 |

*Vacuum applied (<0.5 mm).

EXAMPLE 6

Hyperbranched Polymer form 3,5-Diacetoxybenzoic Acid

Into a 250 ml three-necked round bottom flask equipped with a mechanical stirrer, Wood's metal bath, $N_2$ inlet, and distillation column with vacuum attachment was added 6.00 g (0.025 mol) of 3,5-diacetoxybenzoic acid. The solid reaction ingredient was stirred while the polymerization apparatus was evacuated and purged three times with $N_2$. The stirred, $N_2$ blanketed mixture was then heated to 200° C. with the Wood's metal bath for 17 minutes; the bath temperature was then raised to 271° C. over a period of 37 minutes. Stirring was stopped and the temperature was raised to 325° C. over a period of 14 minutes. A vacuum (0.6 mm) was then applied to the system for 6 minutes when a very viscous melt was obtained. The resulting polymer was allowed to cool under nitrogen. The flask was then broken to recover 3.59 g (81%) of hyperbranched polymer having the following properties:

Tg = 161° C.
Inherent Viscosity = 0.83 (HFIP), 0.17 (THF)
Density = 1.3750 g/cc
Solubility: tetrahydrofuran (THF),
  hexafluoroisopropanol (HFIP),
  dimethylsulfoxide (DMSO),
  dimethylacetamide (DMAC), $CHCl_3$
Decomposition Temperature = 450° C. (TGA)
Ends: 6 COOH ends/$10^6$ g polymer.

The amber polymer was further purified by dissolution in THF followed by addition of a 20:1 excess of water to precipitate the polymer as a white flocculent material.

EXAMPLE 7

Hyperbranched Polymer from 5-Acetoxyisophthalic Acid

Into an apparatus as described in Example 6 was added 6.00 g (0.027 mol) of 5-acetoxyisophthalic acid. The solid reaction ingredient was stirred while the polymerization apparatus was evacuated and purged with $N_2$ three times. The stirred, $N_2$, blanketed material was then heated to 297° C. for 4 minutes. A vacuum (0.2 mm) was then applied to the system for two minutes until a very viscous melt was obtained. The resulting polymer was allowed to cool under nitrogen. The flask was then broken to recover 3.32 g (75%) of hyperbranched polymer which had the following properties:
Tg=269.2° C.
Solubility: $H_2O$ (buffered above pH 7), MeOH, DMSO Inherent Viscosity: 0.05 (methanol), 0.08 (DMSO).

EXAMPLE 8

Hyperbranched Polymer from 4-Bromo-3,5-diacetoxybenzoic Acid

Into an apparatus as described in Example 6 was added 10.0 g (0.0315 mol) of 4-bromo-3,5-diacetoxybenzoic acid. The solid reaction ingredient was stirred while the polymerization apparatus was evacuated and purged with $N_2$ three times. The stirred, $N_2$ blanketed material was then heated to 277° C. for 20 minutes. A vacuum (0.2 mm Hg) was then applied to the system for 2 minutes when a very viscous melt was obtained. The resulting polymer was allowed to cool under nitrogen. The flask was then broken to recover 6.56 g (81%) of hyperbranched polymer having the following properties:

Tg = 147° C.
Inherent Viscosity: 0.09 (HFIP), 0.05 (THF)
Density = 1.6898 g/cc
Solubility: THF, HFIP, DMSO, DMAC,
  o-dichlorobenzene (ODCB), Acetone,
  $CHCl_3$
Ends: 229 COOH ends/$10^6$ g polymer.

EXAMPLE 9

Hyperbranched Polymer from 4,4-Bis(4-acetoxyphenyl)valeric Acid

Into an apparatus as described in Example 6 was added 10.0 g (0.027 mol) of 4,4-bis(4-acetoxyphenyl)- valeric acid and 0.3 g of Sb2O3. The solid reaction ingredients were stirred while the polymerization apparatus was evacuated and purged three times with $N_2$. The stirred, $N_2$ blanketed material was then heated to 227° C. for 3 hours. A vacuum (0.25 mm Hg) was then applied to the system for 10 minutes when a viscous melt was obtained. The resulting polymer was allowed to cool under nitrogen. The flask was then broken to recover 8.23 g (98%) of hyperbranched polymer having the following properties:

Tg = 107° C.
Inherent Viscosity: 0.08 (HFIP), 0.04 (THF)
Density = 1.2361 g/cc
Solubility: HFIP, ODCB, Acetone, $CHCl_3$
Ends: 141 COOH ends/$10^6$ g polymer.

EXAMPLES 10-13

A. Polymerization of $CH_3C(CH_2OH)_2COOH$

Into a three-necked round bottom flask (500 ml) equipped with a mechanical stirrer, Wood's metal bath, $N_2$ and distillation column with vacuum attachment was added 100 g (0.74 mol) of 2,2-bis(hydroxymethyl)-propionic acid and about 0.1-0.2 wt% of "Tyzor" TPT organic titanate as catalyst. The solid reaction ingredients were stirred while the polymerization apparatus was evacuated and purged three times with $N_2$. The stirred, $N_2$ blanketed mixture was then heated to 200° C. with the Wood's metal bath for 3.5 hours. A vacuum was then applied to the system (0.2-0.5 mm Hg) at 200° C. until a viscous melt was obtained (3.5 hours). The resulting polymer was allowed to cool under nitrogen. The flask was then broken to recover 72.4 g (84%) of hyperbranched polyester having the following properties:

| | |
|---|---|
| Tg = 42° C. | |
| Inherent Viscosity = | 0.10 (HFIP), 0.05 (THF), 0.06 (methanol) |
| Solubility: | (3-5% solution, RT); THF, methanol, DMF, N-methylpyrrolidine (NMP), DMAC, Pyridine, Dioxane, HFIP, DMSO, Acetone |
| Ends: 273 COOH ends/$10^6$ g polymer | |
| Branching: | 1 Branch point/2 linear units (determined by $^{13}C$ NMR). |

B. Preparation of Crosslinked HBP-1

Into a 100 ml 3-necked round bottom flask equipped with a reflux condensor, magnetic stirrer, and heating mantle was added the hyperbranched polyester prepared in Part A and 40 ml of THF. The mixture was stirred until all of the polymer dissolved. The solution was divided into 4 parts. To each part was added 1-3 drops of triethylamine and a quantity of a diisocyanate. The mixture was then refluxed overnight. Results were as follows (all yields were over 95%):

| Ex. | HBP (mol) g (mol) | Diisocyanate g (mol) | $\eta$inh | Tg °C. | Comment | Density[e] |
|---|---|---|---|---|---|---|
| 10 | 5 (0.002) | 0.98[a] (0.0054) | — | — | soluble | 1.2760 |
| 11 | 5 (0.002) | 1.40[b] (0.0079) | — | 110 | v. swollen; opalescent gel | 1.2492 |
| 12 | 5 (0.002) | 1.82[b] (0.0104) | — | 125 | insoluble polymer | 1.2463 |
| 13 | 2 (.0008) | 0.34[c] (0.002) | 0.32[d] | 53 | insol THF, sol HFIP | — |

[a]2,4-toluene diisocyanate
[b]2,4-toluene diisocyanate + 1,6-diisocyanate hexane
[c]1,6-diisocyanate hexane
[d]Inherent viscosity in HFIP
[e]Bulk density of cross-linked polyester; bulk density of uncrosslinked polyester: 1.2962.

The crosslinked polymers prepared using toluene diisocyanate or 1,6-hexamethylene diisocyanate, or a mixture thereof, as crosslinking agents can be ground to 200 to 1000 mesh particles and used as packing material for column chromatography or as filtering aids.

EXAMPLE 14

End Capped Hyperbranched Polymer Capping with Acetic Anhydride

Into an apparatus as described for Examples 10-13 was added 1.0 g of finely powdered hyperbranched polyester prepared in Part A of Example 10, 50 ml of acetic anhydride, and 1 drop of sulfuric acid. The mixture was heated to reflux for 1.5 hours. The resulting solution was poured into ice water, extracted sequentially with ether, THF and methylene chloride.

The organic layers were then dried with $MgSO_4$ and evaporated to leave 1.46 g of a very viscous liquid polymer. The polymer had Tg of −64.8° C., Mn = 11,165 (GPC in HFIP, PET standard, Dispersity = 10.1) with 100% of the ends of the polymer being acetyl capped ($^1$HNMR). THe capped polymer was soluble in THF, acetone, HFIP, DMSO, and $CHCl_3$.

EXAMPLE 15

End Capped Hyperbranched Polyester Capping with Maleic Anhydride

Into an apparatus as described in Examples 10-13 was added 0.5 g of the hyperbranched polyester prepared in Part A of Example 10 and 40 ml of dioxane. The mixture was stirred until all of the polymer dissolved. To the solution was added 0.39 g (0.004 mol) of maleic anhydride dissolved in 20 ml of dioxane. The resulting solution was stirred at least 18 hours ar reflux. Removal of all volatiles left 0.43 g of polymer product. The polymer had a Tg of 20.0° C. with 30% of the ends of the polymer being capped ($^1$HNMR). The capped polymer was soluble in MeOH, THF, HFIP, and acetone.

EXAMPLE 16

End Capped Hyperbranched Polyester Capping with Succinic Anhydride

Into an apparatus as described in Examples 10-13 was added 0.5 g of the hyperbranched polyester prepared in Part A of Example 10 and 30 ml of dioxane. The mixture was stirred until all of the polymer dissolved. To the solution was then added 0.40 g (0.004 mol) of succinic anhydride dissolved in 30 ml of THF. Additionally, 0.56 ml (0.004 mol) of triethylamine and 0.03 g of 4-dimethylaminopyridine were added to the mixture. The mixture was then refluxed at least 18 hours. Removal of all volatiles left 0.67 g of capped polymer product. The polymer had thermal transitions at −17.9° C. and −6.0° C. and was soluble in THF.

EXAMPLE 17

End Capped Hyperbranched Polyester Capping with Acid Chloride

Into an apparatus as described in Examples 11–14 was added 0.5 g of the hyperbranched polyester prepared in Part A of Example 10 and 40 ml of THF. The mixture was stirred until all of the polymer dissolved. To the solution was then added equimolar (based on acid chloride ends) quantitites of triethylamine and an acid chloride dissolved in 30 ml of THF. The mixture was then refluxed at least 18 hours. Quantities and yields of capped polyester obtained with specific acid chlorides are shown below.

|  | Yield, g |
| --- | --- |
| Cinnamoyl Chloride 0.66 g (0.004 mol) | 1.06 |
| Malonyl Dichloride 0.17 g (0.0012 mol) | 0.79 |
| N-chlorocarbonylisocyanate 0.42 g (0.0012 mol) | 0.66 |
| Terephthaloylchloride 0.24 g (0.0012 mol) | 0.38 |

EXAMPLE 18

Hyperbranched Copolymer of 2,2-bis(Diacetoxymethyl)-propionic Acid and 3,5-Diacetoxybenzoic Acid Into an apparatus as described in Example 6 was added 10.0 g (0.046 mol) of 2,2-bis(diacetoxymethyl)-propionic acid and 10.9 g (0.046 mol) of 3,5-diacetoxybenzoic acid. The solid reaction ingredients were mixed by stirring while the polymerization apparatus was evacuated and purged with $N_2$ three times. The stirred, $N_2$ blanketed mixture was heated to 227° C. for three hours. A vacuum (0.25 mm Hg) was then applied to the system at 227° C. for 2 hours wherein a very viscous polymer melt was obtained. The polymer was allowed to cool under nitrogen. The flask was then broken and 10.4 g (68%) of hyperbranched copolymer was recovered having the following properties:

| Tg = | −12.9° C. (small), 33.2° C. (large) |
| --- | --- |
| Solubility: | THF, HFIP, DMSO, DMAC, Acetone, $CHCl_3$, o-dichlorobenzene |
| Inherent viscosity: | 0.10 (THF), 0.23 (HFIP) |
| Density: | 1.4605 g/cc. |

EXAMPLE 19

Hyperbranched Copolymer from 2,2-bis(Hydroxymethyl)propionic Acid and 1,1′-Ferrocenedicarboxylic Acid Into apparatus described in Example 6 added 20.0 g (0.149 mol) of 2,2-bis(dihydroxymethyl)-propionic acid and 2.00 g (0.0073 mol) of 1,1′-ferrocenedicarboxylic acid. The solid reaction ingredients were mixed by stirring while the polymerization apparatus was evacuated and purged three times with $N_2$. The stirred $N_2$ blanketed mixture was heated to 200° C. for 2.25 hours. A vacuum (0.6 mm Hg) was then applied to the system at 200° C. for 20 minutes when a viscous polymer melt was obtained. The polymer product was allowed to cool under nitrogen. The flask was then broken and 16.0 g (84%) of hyperbranched copolymer was recovered having the following properties:

Tg=63.7° C.
Solubility: DMSO, DMAC, HFIP
Density: 1.3337 g/cc.

A $^1H$ NMR spectrum of the polymer confirmed the presence of the 1,1′-ferrocenedicarboxylic acid in the polymer.

EXAMPLE 20

Hyperbranched Copolymer from 2,2-bis(Hydroxymethyl)propionic Acid and Hemin 2,2-Bis(hydroxymethyl)propionic acid (20.0 g, 0.149 mol) and 3.0 g (0.0046 mol) of hemin were allowed to react exactly as described in Example 19. The resulting dark-colored copolymer was soluble in THF, hexafluoroisopropanol, acetone, dimethylacetamide, DMSO and methanol. The polymer showed a Tg at 31° C. and a Tm at 76° C. $^1H$ NMR analysis showed the presence of hemin in the soluble portion of polymer.

EXAMPLE 21

Utility—Dispersions of Hyperbranched Polyester 0.5 g of the hyperbranched polyester prepared in Part A of Example 10 was dissolved in 25 ml of ethanol. The solution was divided into five 5 ml portions and water was added as follows:

| 1 | 5 ml | clear solution |
| --- | --- | --- |
| 2 | 12 ml | develops some cloudiness |
| 3 | 18 ml | bluish opalescent disperion |
| 4 | 24 ml | bluish opalescent dispersion |
| 5 | 234 ml | bluish opalescent disperion. |

Addition of 1 drop of 1 N potassium hydroxide solution to the dispersion caused the dispersion to become clear immediately due to decomposition of hyperbranched polyester forming highly water soluble monomer. Addition of 1 drop of concentrated aqueous HCl to the dispersion of hyperbranched polyester caused some clearing and some polymer to coat the sides of the container. Addition of 1 drop of Nujol oil to the dispersion of the hyperbranched polyester precipitated the polymer from the dispersion.

0.5 g of the hyperbranched polyester prepared in Part A of Example 10 was dissolved in 25 ml of THF. The solution was divided into 5 ml portions and various cosolvents were added as follows:

| 1 | Toluene (1.5 ml) | polymer precipitated |
| --- | --- | --- |
| 2 | $CHCl_3$ (1.5 ml) | polymer precipitated |
| 3 | Hexane (1.0 ml) | polymer precipitated |
| 4 | Water (up to 86 ml) | bluish opalescent dispersion. |

Dispersions prepared in water (entry 4 in the above table) showed only very slight settling after standing approximately 6 months. Centrifugation was also ineffective in inducing polymer separation from water.

Light scattering measurements indicated hydrodynamic radii of 1200Å in both ethanol and THF. As the samples were further diluted with $H_2O$, the radii increased to 3000–4000Å but no precipitation was observed.

EXAMPLE 22

Utility—Drug Delivery

A low molecular weight drug was physically suspended in a "pill" prepared from the hyperbranched polymer prepared in Part A of Example 10. The drug diffused out of the pill in less than 24 hours and the integrity of the pill was maintained. Larger molecules (peptides) suspended in the polymer are released more slowly and uniformly as the polymer slowly decomposes. The hyperbranched polyester prepared in Example 10, Part A is biocompatable and its degradation products have very low toxicity. The polymer degrades pH dependently; being most sensistive to aqueous base. Said polyester degrades within minutes in base, but remains stable under acidic conditions for hours to days and remains indefinitely stable under neutral conditions.

EXAMPLE 23

Utility—Rheology Modifier

A 300 g sample of the hyperbranched polyester prepared from 3,5-diacetoxybenzoic acid as in Example 6 was melt blended at a 5% level into a polyarylate. It was observed that the melt viscosity of the overall blend was reduced.

What is claimed is:

1. A polyester prepared by reacting the X and Y functions of a soluble hyperbranched polyester having at least 1 branch per 10 monomer units prepared by conventional polycondensation of one or more monomers of the formula:

$$XR^2[(R^1)_mY]_n$$

wherein:
- $R^1$ is a divalent $C_{1-12}$ hydrocarbyl radical which is linear or branched aliphatic, alicyclic, aromatic or mixed aromatic-aliphatic;
- $R^2$ is a $C_{1-12}$ hydrocarbyl radical having a valence of (n+1), which radical is linear or branched aliphatic, alicyclic, aromatic or mixed aromatic-aliphatic, or $R^2$ is $R^3N$ wherein $R^3$ is defined as for $R^1$; either of $R^1$, $R^2$ or $R^3$ optionally also containing substitutents that are unreactive under processing conditions;
- X and Y are terminal functions selected from —$CO_2R'$ and —$OR\Delta$ wherein R' is H or $C_{1-12}$ alkyl and $R\Delta$ is H or OC(O)R;
- M is 0 or 1; and
- n is an integer and is at least 2:
  with the provisos that:
  (i) both X and Y are not —$CO_2R'$ or —OR";
  (ii) no X or Y function is adjacent to another X or Y function;
  (iii) when $R^2$ is an aliphatic hydrocarbyl radical, Y is —$CO_2R'$; and
  (iv) when $R^2$ is $R^3N$, m is 1; with a difunctional reagent.

2. The polyester of claim 1 wherein the X and Y functions have been reacted with a diisocyanate.

3. The polyester of claim 2 wherein sufficient diisocyanate is reacted to create a linearly linked polyester.

4. The polyester of claim 2 wherein sufficient diisocyanate is reacted to create a nodular network polyester.

5. A polyester prepared by reacting the X and Y functions of a soluble hyperbranched polyester having at least one branch per 10 monomer units, said polyester being prepared by conventional polycondensation of one or more monomers of the formula:

$$XR^2[(R^1)_mY]_n$$

wherein
- $R^1$ is a divalent $C_{1-12}$ hydrocarbyl radical which is linear or branched aliphatic, alicyclic, aromatic or mixed aromatic-aliphatic;
- $R^2$ is a $C_{1-12}$ hydrocarbyl radical having a valence of (n+1), which radical is linear or branched aliphatic;
- either of $R^1$ or $R^2$ optionally also containing substituents that are unreactive under processing conditions;
- X is $CO_2R'$;
- Y is $OR\Delta$, wherein R' is H or $C_{1-12}$ alkyl and R" is H or OC(O)R';
- m is 0 or 1; and
- n is an integer and is at least 2; with the proviso that:
  (i) no X or Y function is adjacent to another X or Y function with a difunctional reagent.

6. The polyester X and Y of claim 5 wherein the X and Y functions have been reacted with a diisocyanate.

7. The polyester of claim 6 wherein sufficient diisocyanate is reacted to create a linearly linked polyester.

8. The polyester of claim 6 wherein sufficient diisocyanate is reacted to create a nodular network polyester.

* * * * *